(12) United States Patent
Hayashi et al.

(10) Patent No.: US 9,347,041 B2
(45) Date of Patent: May 24, 2016

(54) METHOD FOR PREPARING CORNEAL ENDOTHELIAL CELL

(75) Inventors: Ryuhei Hayashi, Osaka (JP); Susumu Hara, Osaka (JP); Tomofumi Kageyama, Osaka (JP); Kohji Nishida, Osaka (JP)

(73) Assignee: OSAKA UNIVERSITY, Osaka (JP)

( * ) Notice: Subject to any disclaimer, the term of this patent is extended or adjusted under 35 U.S.C. 154(b) by 0 days.

(21) Appl. No.: 14/233,056

(22) PCT Filed: Jul. 13, 2012

(86) PCT No.: PCT/JP2012/068538
§ 371 (c)(1),
(2), (4) Date: Jan. 15, 2014

(87) PCT Pub. No.: WO2013/012087
PCT Pub. Date: Jan. 24, 2013

(65) Prior Publication Data
US 2014/0170751 A1 Jun. 19, 2014

(30) Foreign Application Priority Data
Jul. 15, 2011 (JP) ................................ 2011-156641

(51) Int. Cl.
*C12N 5/02* (2006.01)
*C12N 5/079* (2010.01)
*A61K 35/30* (2015.01)

(52) U.S. Cl.
CPC .............. *C12N 5/0621* (2013.01); *A61K 35/30* (2013.01); *C12N 2501/115* (2013.01); *C12N 2501/48* (2013.01); *C12N 2533/52* (2013.01); *C12N 2533/54* (2013.01); *C12N 2533/90* (2013.01)

(58) Field of Classification Search
None
See application file for complete search history.

(56) References Cited

U.S. PATENT DOCUMENTS

| 2007/0092550 | A1 | 4/2007 | Lui |
| 2007/0148137 | A1 | 6/2007 | Okano et al. |
| 2007/0275365 | A1 | 11/2007 | Lui |
| 2009/0232772 | A1 | 9/2009 | Amano et al. |
| 2010/0003299 | A1 | 1/2010 | Tseng et al. |
| 2013/0023050 | A1 | 1/2013 | Shima et al. |

FOREIGN PATENT DOCUMENTS

| EP | 1600177 | A1 | 11/2005 |
| EP | 2383334 | A1 | 11/2011 |
| JP | 2003-038170 | A | 2/2003 |
| JP | 2006-187281 | A | 7/2006 |
| JP | 2007-508015 | A | 4/2007 |
| JP | 2007-509643 | A | 4/2007 |
| JP | 2009-268433 | A | 11/2009 |
| JP | 2010-505001 | A | 2/2010 |
| WO | 2004/073761 | A1 | 9/2004 |
| WO | 2006092894 | A1 | 9/2006 |
| WO | WO 2006092894 | A1 * | 9/2006 |
| WO | 2010/084970 | A1 | 7/2010 |
| WO | 2011/096593 | A1 | 8/2011 |

OTHER PUBLICATIONS

Jackel et al., "Serum-free corneal organ culture medium (SFM) but not conventional minimal essential organ culture medium (MEM) protects human corneal endothelial cells from apoptotic and necrotic cell death", British Journal of Ophthalmology 2011, vol. 95, pp. 123-130.*
Yamaguchi et al., "Adhesion, Migration, and Proliferation of Cultured Human Corneal Endothelial Cells by Laminin-5", Investigative Ophthalmology & Visual Science 2011, vol. 52, pp. 679-684.*
Okumura et al., "Enhancement on Primate Corneal Endothelial Cell Survival In Vitro by a Rock Inhibitor", Investigative Ophthalmology & Visual Science 2009, vol. 50, pp. 3680-3687.*
Zhu et al., "Characterization and Comparison of Intracellular Adherent Junctions Expressed by Human Corneal Endothelial Cells in Vivo and In Vitro", Investigative Ophthalmology & Visual Science 2008, vol. 49, pp. 3879-3886.*
Proulx et al., "Methods being developed for preparation, delivery and transplantation of a tissue-engineered corneal endothelium", Experimental Eye Research 2012, vol. 95, pp. 68-75.*
Madden, P.W., et al., "Human corneal endothelial cell growth on a silk fibroin membrane," Biomaterials, vol. 32, No. 17, Jun. 1, 2011, pp. 4076-4084. Mimura, T. et al., "Sphere therapy for corneal endothelium deficiency in a rabbit model," Investigative Ophthalmology & Visual Science, vol. 46, No. 9., Sep. 2005, pp. 3128-3135.
Extended European Search Report issued by European Patent Office in European Patent Application 12815195.8 (PCT/JP2012068538), dated Dec. 19, 2014.
Yamamoto, N. et al, "Basic study of retinal stem/progenitor cell separation from mouse iris tissue", Med Mol Morphol, 2010, vol. 43, No. 3, p. 139-144.
Tadashi Senoo et al., "Suihosei Kakumakusho no Kakumaku Naihi Saibo Zoshokuno", Journal of Japanese Ophthalmological Society, 2001, vol. 105, p. 196, p. 65 with English translation thereof.

(Continued)

*Primary Examiner* — Renee Claytor
*Assistant Examiner* — Michelle F Paguio Frising
(74) *Attorney, Agent, or Firm* — Pearne & Gordon LLP (57) ABSTRACT

The present invention relates to a method for preparing corneal endothelial progenitor cells by adherent culturing a cell population isolated from corneal endothelial cell tissue at a low density by using a serum-free medium. The present invention also relates to a method for preparing corneal endothelial cells by differentiation-inducing the corneal endothelial progenitor cells obtained by the aforementioned method. According to the present invention, corneal endothelial progenitor cells can be selectively grown from a corneal tissue-derived cell population, and corneal endothelial cells obtained by inducing the corneal endothelial progenitor cells can be applied to treatment of corneal endothelial diseases. As a result, problems of corneal transplantation such as shortage of donors and occurrence of rejection can be solved.

14 Claims, 8 Drawing Sheets
(3 of 8 Drawing Sheet(s) Filed in Color)

(56) References Cited

OTHER PUBLICATIONS

Michiharu Kikuchi et al., "Suihosei Kakumakusho ni Okeru Kakumaku Naihi Saibo no Zoshokuno", Journal of Japanese Ophthalmological Society , 2002, vol. 106, p. 103, 47 with English translation thereof.

Yoshida S, et al., "Isolation of multipotent neural crest-derived stem cells from the adult mouse cornea", Stem Cells. 2006, vol. 24, No. 12, p. 2714-22.

Ide T, et al., "Structural characterization of bioengineered human corneal endothelial cell sheets fabricated on temperature-responsive culture dishes," Biomaterials, Feb. 2006, 27 (4): 607-614.

Zhu C and Joyce NC, "Proliferative response of corneal endothelial cells from young and older donors," Invest Ophthalmol Vis Sci., Jun. 2004, 45(6): 1743-1751.

Yokoo S. et al., "Human corneal endothelial cell precursors isolated by sphere-forming assay," Invest Ophthalmol Vis Sci., May 2005, 46(5): 1626-1631.

Hirata-Tominaga et al., "Corneal endothelial cell fate is maintained by LGR5 through the regulation of hedgehog and Wnt pathway," Stem Cells, 2013, 31: 1396-1407.

Li et al., "A novel method of isolation, preservation, and expansion of human corneal endothelial cells," Investigative Ophthalmology & Visual Science, 2007, 48(2): 614-620.

Yamagami et al., "Distribution of precursors in human corneal stromal cells and endothelial cells," Ophthalmology, 2007, 114(3): 433-439.

International Search Report for application No. PCT/JP2012/068538 dated Oct. 16, 2012.

* cited by examiner

METHOD FOR PREPARING CORNEAL ENDOTHELIAL CELL

TECHNICAL FIELD

The present invention relates to a method for selectively growing corneal endothelial progenitor cells from a cell population isolated from corneal endothelial tissue, and a method for obtaining corneal endothelial cells from the corneal endothelial progenitor cells grown by the aforementioned method.

BACKGROUND ART

A cornea includes five layers of a corneal epithelia layer, a Bowman's membrane, a corneal stromal layer, a Descemet's membrane and a corneal endothelial layer provided in this order from the outside. The corneal endothelial layer present in the innermost position among these layers is a single cell layer, and keeps the corneal thickness constant by taking a substance necessary for the cornea from aqueous humor and discharging fluid of the cornea to the aqueous humor, so as to retain the transparency of the cornea. If the number of corneal endothelial cells is reduced, the fluid cannot be sufficiently discharged, which leads to corneal opacity or a corneal endothelial disease such as bullous keratopathy.

In general, human corneal endothelial cell density is approximately 3000 cells/mm$^2$, but it is lowered to approximately 500 cells/mm$^2$ in a patient suffering from a corneal endothelial disease. However, the human corneal endothelial cells are not grown in vivo, and hence, if they are damaged or largely reduced once, the only basic treatment is transplantation.

A refractory corneal endothelial disease such as bullous keratopathy has been conventionally treated by penetrating keratoplasty, but this treatment has problems of absolute shortage of donors and rejection occurring after the transplantation. In order to reduce the rejection, a method in which a corneal endothelium (partly including corneal stromal cells) of an imported human eye bank cornea is collected to be transplanted to a diseased eye (Descement stripping endothelial keratoplasty: DSEK) has been employed, but the problem of shortage of donors still cannot be overcome by the DSEK.

A method in which corneal endothelial cells are grown in vitro to be used for a treatment has been tried (for example, Non-patent Literature 1 and Patent Literatures 1 and 2). In a conventional culture method using a serum, however, corneal endothelial cells are changed in cell shape to lose the corneal endothelial function through long-term culture, and ultimately, the growth is completely stopped, and hence, the cells can be generally grown merely up to a passage number of 5 to 7 (Non-patent Literature 2). This is probably because, in an existing method, corneal endothelial progenitor cells cannot be selectively grown and hence differentiated cells alone are temporarily grown.

It has been reported that a sphere obtained by suspension culture of corneal endothelial cells has properties of a corneal endothelial progenitor cell (Non-patent Literature 3 and Patent Literature 3). The sphere thus obtained does not, however, express p75, a marker for neural crest stem cells, which are an origin of a corneal endothelium, and its undifferentiation is unknown. P75 is expressed in merely stem cells, including neural crest stem cells, present in vivo in a small number, and is one of markers the most reliable as an index of undifferentiation.

As described so far, under the present condition, although there is a technology to grow mature cultured corneal endothelial cells, the transplantation of the cultured corneal endothelial cells is not performed. Therefore, it is desired to develop a technique to obtain and grow corneal endothelial stem cells or corneal endothelial progenitor cells, which can be stably grown to be induced into corneal endothelial cells with good quality.

CITATION LIST

Patent Literature

Patent Literature 1: WO2004/073761
Patent Literature 2: Japanese Patent Laid-Open No. 2003-038170
Patent Literature 3: Japanese Patent Laid-Open No. 2006-187281

Non-Patent Literature

Non-patent Literature 1: Ide T, et al., Biomaterials, 2006 Feb. 27(4):607-614
Non-patent Literature 2: Zhu C and Joyce N C, Invest Ophthalmol Vis Sci., 2004 June, 45(6):1743-1751
Non-patent Literature 3: Yokoo S. et al., Invest Ophthalmol Vis Sci., 2005 May, 46 (5):1626-1631

SUMMARY OF INVENTION

Technical Problem

An object of the present invention is to solve the problems of shortage of donors and occurrence of rejection in corneal transplantation by selectively growing, from a corneal tissue-derived cell population, undifferentiated corneal endothelial progenitor cells, and by applying corneal endothelial cells induced therefrom to a treatment of a corneal endothelial disease.

Solution to Problem

The present inventors have found the following: When a cell population isolated by an enzymatic treatment from corneal endothelial tissue is cultured at a low density for a long period of time by using a specific serum-free culture medium, corneal endothelial progenitor cells can be selectively grown.

Specifically, the present invention relates to a method for preparing corneal endothelial progenitor cells in which a cell population isolated from corneal endothelial cell tissue is adherent cultured at a low density by using a serum-free medium.

The culture is performed with cells seeded at a density of at least lower than 10000 cells/cm$^2$, preferably 5000 cells/cm$^2$ or lower, more preferably 20 to 2000 cells/cm$^2$, further more preferably 50 to 1000 cells/cm$^2$, and most preferably approximately 100 to 500 cells/cm$^2$.

According to the method of the present invention, an undifferentiated corneal endothelial progenitor cell population having high proliferation ability is selectively grown. The corneal endothelial progenitor cell population characterized by being positive for a neural crest marker p75, used as an index of undifferentiation is grown, and in addition, neural crest markers FOXC2 and SOX9 and a corneal endothelium marker N-cadherin are also expressed therein. These markers are highly expressed at the beginning of the culture, but gradually disappear as the growth progresses. On the other hand, the grown cell population starts to highly express a growth marker Ki-67, which is not expressed at the initial stage of the culture, and shows extremely high proliferation ability, so that a single cell can be ultimately grown to at least $1 \times 10^5$ cells or more.

The medium used in the present invention preferably contains at least one or more cytokines selected from bFGF, EGF, TGF, NGF and Wn3a.

The medium may contain a serum replacement such as KSR. Furthermore, the medium may contain one or more selected from retinoic acid, β mercaptoethanol, sodium pyruvate and ascorbic acid.

The adherent culture is performed by using a culture vessel coated with collagen, laminin, fibronectin, Matrigel™, poly-L-ornithine/laminin, or poly-D-lysine (PDL).

According to the method of the present invention, corneal endothelial progenitor cells with high proliferation ability can be cultured in an undifferentiated state for a long period of time. Preferably, the culture is performed continuously for 7 or more days.

The origin of the used corneal endothelial cell tissue is not limited but it is preferably human origin.

The corneal endothelial progenitor cells can be obtained by isolating a p75-positive cell population from the cell population cultured by the aforementioned method.

The present invention also provides a method for preparing corneal endothelial cells in which the corneal endothelial progenitor cell population prepared by the aforementioned method is differentiation-induced into a corneal endothelial cell population.

The differentiation induction into a corneal endothelial cell population can be performed by using, for example, a serum-free medium containing TGF-$\beta_2$ or a medium containing a serum.

The differential induction into a corneal endothelial cell population can be performed by the adherent culture using a culture dish (vessel) coated with collagen, laminin, fibronectin, Matrigel™, poly-L-ornithine/laminin (PLO/LM), poly-D-lysine (PDL) or the like, and if a corneal endothelial cell sheet described later is to be produced, the corneal endothelial progenitor cells may be cultured on a polymer membrane to be differentiation-induced into corneal endothelial cells.

Furthermore, the present invention provides a method for producing a corneal endothelial cell sheet by culturing the corneal endothelial progenitor cell population or corneal endothelial cell population prepared by the method of the present invention with a polymer membrane used as a carrier.

An example of the polymer membrane to be used includes a membrane containing one or more selected from the group consisting of glycosaminoglycan such as chondroitin sulfate, dermatan sulfate, hyaluronate, heparan sulfate, heparin and keratan sulfate; atelocollagen, alkali-treated collagen, and gelatin; keratin; proteoglycan; alginate, chitosan and hyaluronate; polyamino acids (polylactic acid); cellulose; temperature responsive polymers such as (meth)acrylamide compounds, N-(or N,N-di)alkyl-substituted (meth)acrylamide derivatives, vinyl ether derivatives and copolymers of these.

Advantageous Effect of Invention

According to the present invention, cells derived from corneal endothelial tissue can be grown in a more undifferentiated state (while keeping a p75-positive state). In other words, according to the present invention, a more undifferentiated cell population (corneal endothelial progenitor cells) can be selectively grown and isolated from cells derived from corneal endothelial tissue. The corneal endothelial progenitor cell population obtained by the present invention has high proliferation ability and hence can be passage cultured for a long period of time, and hence, a larger number of corneal endothelial progenitor cell populations can be prepared.

When the corneal endothelial progenitor cell population obtained by the present invention is cultured under suitable conditions, it can be differentiation-induced into mature corneal endothelial cells. Therefore, according to the present invention, a corneal endothelial cell source stable for a long period of time can be supplied, which can solve the problem of serious shortage of donors (with 10 million patients on the waiting list) in the cornea tissue engineering.

BRIEF DESCRIPTION OF DRAWINGS

The patent or application file contains at least one drawing executed in color. Copies of this patent or patent application publication with color drawing(s) will be provided by the Office upon request and payment of the necessary fee.

FIG. 1 FIGS. 1A and 1B illustrate cells obtained from corneal endothelial tissue by a method of the present invention (specifically, FIG. 1A illustrates primary culture on day 14 and FIG. 1B illustrates primary culture on day 21).

FIG. 4 FIGS. 4A, 4B and 4C illustrate proliferation ability of the corneal endothelial progenitor cells obtained by the method of the present invention.

FIG. 5 FIG. 5A illustrates images of corneal endothelial cells differentiated from the corneal endothelial progenitor cells obtained by the method of the present invention (specifically, the corneal endothelial progenitor cells obtained by the method of the present invention (left) and ordinarily cultured corneal endothelial cells (right)). FIG. 5B illustrates expression of a corneal endothelial marker, type VIII collagen (COL8A2) (in the corneal endothelial progenitor cells, the corneal endothelial cells differentiated from the corneal endothelial progenitor cells, cells obtained by a known method, and corneal endothelial cells present in vivo in this order from the left).

FIG. 6 FIGS. 6A to 6F illustrate analysis results of a corneal endothelial cell sheet prepared on an atelocollagen sheet (specifically, FIG. 6A illustrates a corneal endothelial cell sheet prepared on an atelocollagent sheet, FIG. 6B illustrates a phase contrast image, FIG. 6C illustrates an alizarin-stained image, FIG. 6D illustrates expression of $Na^+/K^+$-ATPase, FIG. 6E illustrates expression of ZO-1, and FIG. 6F illustrates expression of N-cadherin).

FIG. 7 FIGS. 7A and 7B illustrate results of analysis of a pump function of a corneal endothelial cell sheet by an in vitro evaluation system (ussing-chamber system) (specifically, FIG. 7A illustrates change over time of a short-circuit current, and FIG. 7B illustrates comparison of the short-circuit current between the corneal endothelial cells differentiated from the corneal endothelial progenitor cells (left) and cultured corneal endothelium (right).

FIG. 8 FIGS. 8A and 8B illustrate results of verification performed in a rabbit bullous keratopathy model having a corneal endothelial cell sheet transplanted, and specifically.

The entire contents of Japanese Patent Application No. 2011-156641, to which this application claims the benefit of priority, are incorporated herein by reference.

DESCRIPTION OF EMBODIMENT

1. Definitions

Terms used in the present invention will now be described.

(1) Corneal Endothelial Cells

A cornea has a three-layered structure consisting of a corneal epithelia layer, a corneal stromal layer and a corneal endothelium layer provided in this order from the surface side. "Corneal endothelial cells" are a cell population forming the innermost layer of the cornea, and are not regenerated in vivo when damaged. The "corneal endothelial cells" are derived from a neural crest, are in a cobblestone like shape, and are characterized by expression of differentiation markers for the corneal endothelial cells, type VIII collagen, ZO-1, $Na^+/K^+$ ATPase, and the like.

(2) Corneal Endothelial Progenitor Cells

"Corneal endothelial progenitor cells" of the present invention mean undifferentiated cells that can be differentiated into a corneal endothelium. The "corneal endothelial progenitor cells" are cells in a dendritic shape and have high proliferation ability. Besides, at the initial stage of culture (growth), they do not express a differentiation marker but are characterized by expression of p75, that is, a marker specific to undifferentiated cells such as neural crest stem cells. There is possibility that the "corneal endothelial progenitor cells" obtained in the present invention also have properties as stem cells (multipotency and self-renewal ability). In that sense, the "corneal endothelial progenitor cells" can be described as "corneal endothelial stem cells/progenitor cells".

(3) Serum-Free Medium

A "serum-free medium" used in the present invention means a medium not containing serum components of other species. In using a serum-free medium, there is no fear of infection with a pathogen derived from an animal serum, and therefore, resultant cells or culture can be safely used in clinical application. Therefore, in consideration of application of the corneal endothelial cells obtained in the present invention to tissue engineering or the like, a serum-free medium is preferably used as the medium. Incidentally, a serum-free medium may contain an artificial serum replacement described below.

(4) Serum Replacement

A "serum replacement" used in the present invention means an artificial serum replacement usable instead of a serum, and examples include KSR (knockout serum replacement: manufactured by Invitrogen (GIBCO)) mentioned above, albumin such as lipid rich albumin, transferrin, fatty acid, insulin, collagen precursors, trace elements, 2-mercaptoethanol and 3'-thiol glycerol, and equivalents of these.

(5) Cytokine

"Cytokine" is a generic name for proteinous factors released from cells and mediating various cellular interactions. In the present invention, cytokine is added to a medium in order to accelerate the growth and the differentiation induction of cells.

Examples of the "cytokine" used in the present invention include a basic fibroblast growth factor (bFGF), a transforming growth factor-$\beta$ (TGF-$\beta$ (including TGF-$\beta_1$, TGF-$\beta_2$, TGF-$\beta_3$, etc.), interferons (such as IFN$\alpha$, IFN$\beta$ and IFN$\gamma$), interleukins, a vascular endothelial growth factor (VEGF), thrombopoietin (TPO), a granulocyte-colony stimulating factor (G-CSF), a Macrophage-colony stimulating factor (M-CSF), and a nerve growth factor (NGF), and the cytokine is not limited to these examples as long as it is suitable to the object and the effect of the present invention.

(6) Cell Marker

In the present invention, in order to identify the corneal endothelial progenitor cells and the corneal endothelial cells differentiation-induced therefrom, proteins (cell markers) specifically expressed in the respective cell strains are used. Specifically, at the initial stage of the culture, the corneal endothelial progenitor cell population of the present invention is determined by being positive for p75, FOXC2, SOX9 and N-cadherin. These markers can be retained in the culture system of the present invention for a prescribed period of time, but gradually disappear as the growth progresses. On the other hand, the corneal endothelial progenitor cells do not express Ki-67 at the initial stage of the culture but highly expresses Ki-67 at the time of growth. On the other hand, a cell population containing the differentiation-induced corneal endothelial cells is determined by being positive for type VIII collagen.

P75, that is, a nerve growth factor receptor and a receptor for neurotrophins, is known as a low affinity neurotrophin receptor, and is used as a marker for migrating neural crest cells. P75 is expressed in merely stem cells, including the neural crest stem cells, present in a small number in vivo, and is one of markers the most reliable as an index of undifferentiation. As the markers for the neural crest cells, FOXC2 (Forkhead box protein C2), SOX9, SOX10, AP2$\beta$, AB2$\alpha$, snail, slug, PITX2, FOXC1 and the like are also known.

N-cadherin is a protein belonging to calcium-dependent cell adhesion molecules, and is known to play a significant role in cell adhesion through a bond to an actin cytoskeleton through interaction of allogenic cadherin and catenin, and to affect a development/differentiation stage. N-cadherin is a mesenchymal marker expressed in various tissues such as nerves, heart muscle, skeletal muscle, vascular endothelia and corneal endothelia.

Type VIII collagen is nonfibrillar collagen, is largely expressed in morphogenetically active tissues, and is known as a marker for differentiated corneal endothelial cells. Another example of the marker for differentiated corneal endothelial cells includes ZO-1.

2. Cell Culture Method—Method for Selectively Growing Corneal Endothelial Progenitor Cell Population 2.1 Isolation of Cells First, isolated corneal endothelial tissue is treated with an enzyme such as trypsin or collagenase by an ordinary method to isolate cells. The isolated cells are suspended in a basal medium such as DMEM, followed by centrifugation for removing tissue pieces. The thus prepared cell population derived from the corneal endothelial tissue is cultured as follows.

2.2 Cell Culture

Principal characteristics of the method of the present invention are (1) a serum-free medium, (2) low-density culture and (3) adherent culture.

(1) Medium Composition (Serum-Free Medium)

In the method of the present invention, a serum-free medium containing no serum is used for culturing cells. A basal medium can be any medium that can be used for culturing animal cells, such as a DMEM medium, a BME medium, a BGJb medium, a CMRL 1066 medium, a Glasgow MEM medium, an Improved MEM Zinc Option medium, an IMDM medium, a Medium 199 medium, an Eagle MEM medium, an α MEM medium, a Dulbecco MEM medium, a HAM medium, a RPMI 1640 medium, a Fischer's medium, a McCoy's medium, a Williams E medium, or a mixed medium of these.

A medium used in the culture method of the present invention is prepared by adding, to the above-described basal medium, various nutrients necessary for maintenance and growth of cells and various components necessary for differentiation induction. The medium preferably contains a cytokine or a serum replacement for stimulating the growth of the cells. Examples of the cytokine to be contained in the medium include a basic fibroblast growth factor (bFGF), a transforming growth factor-β (TGF-β), interferons (such as IFNα, IFNβ and IFNγ), interleukins, a vascular endothelial growth factor (VEGF), thrombopoietin (TPO), a granulocyte-colony stimulating factor (G-CSF), a Macrophage-colony stimulating factor (M-CSF), and a nerve growth factor (NGF).

Examples of the serum replacement include albumin (such as lipid rich albumin), transferrin, fatty acid, insulin, collagen precursors, trace elements, β-mercaptoethanol, 3'-thiol glycerol, and commercially available products of Knockout Serum Replacement (KSR), Chemically-defined Lipid concentrated (manufactured by Gibco) and Glutamax (manufactured by Gibco).

Besides, pyruvic acid, an amino acid reducing agent such as β-mercaptoethanol, amino acid, or the like can be added to the medium as occasion demands.

In addition to the above, the medium can contain, as nutrients, a carbon source such as glycerol, glucose, fructose, sucrose, lactose, honey, starch or dextrin; a hydrocarbon such as fatty acid, fats and oils, lecithin or alcohols; a nitrogen source such as ammonium sulfate, ammonium nitrate, ammonium chloride, urea or sodium nitrate; an inorganic salt such as sodium chloride, potassium salt, phosphate, magnesium salt, calcium salt, iron salt or manganese salt; monopotassium phosphate, dipotassium phosphate, magnesium sulfate, sodium chloride, ferrous sulfate, sodium molybdate, sodium tungstate, manganese sulfate, various vitamins or the like.

The medium obtained by mixing these components has pH of 5.5 to 9.0, preferably 6.0 to 8.0 and more preferably 6.5 to 7.5.

(2) Low-Density Culture

In culture of corneal endothelial cells, in general, cells are seeded or are explant cultured with the Descemet's membrane inclusive at a high density of 10,000 to 100,000 cells/$cm^2$. In the method of the present invention, however, the culture is performed with cells seeded at a low density of lower than at least 10000 cells/$cm^2$, preferably 5000 cells/$cm^2$ or lower, more preferably 20 to 2000 cells/$cm^2$, further more preferably 50 to 1000 cells/$cm^2$, and most preferably approximately 100 to 500 cells/$cm^2$.

(3) Adherent Culture

In the method of the present invention, a culture dish (vessel) coated with collagen, laminin, fibronectin, Matrigel™, poly-L-ornithine/laminin (PLO/LM), poly-D-lysine (PDL) or the like is used for performing adherent culture.

The culture is performed under the aforementioned conditions at 36° C. to 38° C. and preferably 36.5° to 37.5° C. under a condition of 1% to 25% $O_2$ and 1% to 15% $CO_2$. With the medium exchanged every 2 to 3 days, the culture is performed for at least 7 days and preferably for 7 to 14 days.

2.3 Selective Growth of Corneal Endothelial Progenitor Cell Population

In a conventional method using a medium containing a serum, the cell shape is changed as culture passages are made, and hence it becomes difficult to retain the corneal endothelial function and the proliferation ability. In the method of the present invention, however, the cell shape is not changed even when culture passages are made, and hence, the culture can be performed for a long period of time with the proliferation ability kept high. This is because the cells derived from the corneal endothelial tissue can be grown while keeping the undifferentiated state in the method of the present invention. In other words, in the method of the present invention, a more undifferentiated cell population having high proliferation ability can be selectively grown.

The corneal endothelial progenitor cell population selectively grown in the present invention is distinguished, in a point that it is positive for the undifferentiation marker p75, from a corneal endothelium-derived cell population cultured by a conventionally known method. Although the expression of p75 gradually disappears as the growth progresses, such a cell population has high proliferation ability and hence can be grown ultimately to 100000-fold.

This cell population is distinguished from the corneal endothelium-derived cell population cultured by the conventionally known method also in a point that the neural crest markers SOX9 and FOXC2 are expressed at the beginning of the culture and the corneal endothelial marker N-cadherin is also expressed. The expressions of SOX9, FOXC2 and N-cadherin also gradually disappear as the growth progresses.

The corneal endothelial progenitor cell population grown by the method of the present invention is a cell population having an excessively high proliferation ability that expresses the growth marker Ki-67 and has such high proliferation ability that a single cell can be ultimately grown to $1 \times 10^5$ cells or more. This cell population can be differentiated into corneal endothelial cells under suitable conditions. In the present invention, this cell population that can be differentiated into corneal endothelial cells is designated as the "corneal endothelial progenitor cell (population)".

3. Differentiation Induction of Corneal Endothelial Progenitor Cells to Corneal Endothelial Cells As described above, the corneal endothelial progenitor cell population obtained by the method of the present invention can be differentiated into mature corneal endothelial cells by culturing it under suitable conditions.

(1) Medium Composition

A basal medium can be any medium that can be used for culturing animal cells, such as a DMEM medium, a BME medium, a BGJb medium, a CMRL 1066 medium, a Glasgow MEM medium, an Improved MEM Zinc Option medium, an IMDM medium, a Medium 199 medium, an Eagle MEM medium, an a MEM medium, a Dulbecco MEM medium, a HAM medium, a RPMI 1640 medium, a Fischer's medium, a McCoy's medium, a Williams E medium or a mixed medium of these.

The medium used for the differentiation induction to the corneal endothelial cells is prepared by adding, to the above-described basal medium, a factor for stimulating the differentiation induction to the corneal endothelial cells, various nutrients necessary for maintenance and growth of the cells and various components necessary for the differentiation induction.

Examples of the factor for stimulating the differentiation induction to the corneal endothelial cells include TGF-$\beta_2$, cholera toxin, transferrin, insulin, EGM (Epidermal Growth Factor), and a serum or a serum replacement, KSR (Knockout Serum Replacement).

Preferably, a serum-free medium containing TGF-$\beta_2$ (see Japanese Patent Laid-Open No. 2009-268433) or a medium containing a serum such as BSA is used for the differentiation induction to the corneal endothelial cells.

Besides, an antibiotic such as penicillin or streptomycin, a cytokine, pyruvic acid, an amino acid reducing agent such as β-mercaptoethanol, an antioxidant such as ascorbic acid, amino acid, or the like can be added to the medium as occasion demands.

In addition to the above, the medium can contain, as nutrients, a carbon source such as glycerol, glucose, fructose, sucrose, lactose, honey, starch or dextrin; a hydrocarbon such as fatty acid, fats and oils, lecithin or alcohols; a nitrogen source such as ammonium sulfate, ammonium nitrate, ammonium chloride, urea or sodium nitrate; an inorganic salt such as sodium chloride, potassium salt, phosphate, magnesium salt, calcium salt, iron salt or manganese salt; monopotassium phosphate, dipotassium phosphate, magnesium sulfate, sodium chloride, ferrous sulfate, sodium molybdate, sodium tungstate, manganese sulfate, various vitamins and the like.

The medium obtained by mixing these components has pH of 5.5 to 9.0, preferably 6.0 to 8.0 and more preferably 6.5 to 7.5.

(2) Culture Conditions

The culture is performed by using a culture dish (vessel) coated with collagen, laminin, fibronectin, Matrigel™, poly-L-ornithine/laminin (PLO/LM), poly-D-lysine (PDL) or the like at 36° C. to 38° C. and preferably 36.5° to 37.5° C. under a condition of 1% to 25% $O_2$ and 1% to 15% $CO_2$. With the medium exchanged every 2 to 3 days, the culture is performed for at least 7 days and preferably for approximately 1 to 8 weeks.

The differentiation induction of the corneal endothelial progenitor cell population to the mature corneal endothelial cells can be confirmed by change in shape (change to cells in a cobblestone like shape) and the expression of the mature corneal endothelial cell marker, type VIII collagen or the like.

4. Purification of Cells

The corneal endothelial progenitor cell population grown by the method of the present invention can be easily isolated (purified) by using a surface marker, p75 or the like. The cells can be isolated by separation using, for example, immunomagnetic beads labeled with a p75-specific antibody, a column in which a p75 antibody is immobilized, or a cell sorter (FACS) using a fluorescent labeled p75 antibody.

Furthermore, the corneal endothelial cell population differentiation-induced by the method of the present invention can be isolated by using, as an index, the expression of the marker, type VIII collagen or the like, which is not a surface marker but a marker specific to the corneal endothelial cells.

5. Application to Tissue Engineering 5.1 Culture

A culture containing the corneal endothelial progenitor cell population obtained by the method of the present invention and/or the corneal endothelial cell population differentiation-induced from the aforementioned cell population can be used for studies, the tissue engineering or as a material of a cell preparation described later.

5.2 Cell Preparation for Treatment of Corneal Endothelial Disease

The corneal endothelial progenitor cell population differentiation-induced and isolated by the method of the present invention and/or the corneal endothelial cell population differentiation-induced from the aforementioned cell population can be used as a cell preparation for a corneal endothelial disease.

A method for administering the cell preparation of the present invention is not especially limited, and it can be administered by local transplantation with surgical means, intravenous administration or local injection administration in accordance with an application site.

The cell preparation of the present invention may contain a scaffolding material or a component for assisting the maintenance/growth of the cells and the administration to a patient, and a pharmaceutically acceptable carrier.

Examples of a component necessary for the maintenance/growth of the cells include medium components such as a carbon source, a nitrogen source, vitamins, minerals, salts and various cytokines, and an extracellular matrix preparation such as Matrigel™.

The cell preparation of the present invention may contain a scaffolding material or a component for assisting the maintenance/growth of the cells and the administration to a patient, and a pharmaceutically acceptable carrier.

Examples of a component necessary for the maintenance/growth of the cells include medium components such as a carbon source, a nitrogen source, vitamins, minerals, salts and various cytokines, and an extracellular matrix preparation such as Matrigel™.

Examples of a scaffolding material or a component for assisting the administration to a patient include a biodegradable polymer such as collagen, polylactic acid, hyaluronate, cellulose, a derivative of any of these, or a complex of two or more of these; and an injectable aqueous solution such as a saline, a medium, a biological buffer such as PBS, or an isotonic solution containing glucose or another adjuvant (such as D-sorbitol, D-mannose, D-mannitol or sodium chloride), and can be used together with an appropriate solubilizing agent, for example, alcohol such as ethanol, polyalcohol such as propylene glycol or polyethylene glycol, or a nonionic detergent such as polysorbate-80 and HCO-50.

In addition, the cell preparation may contain, as occasion demands, a pharmaceutically acceptable organic solvent, polyvinyl alcohol, polyvinyl pyrrolidone, a carboxyvinyl polymer, carboxymethyl cellulose sodium, sodium polyacrylate, sodium alginate, water-soluble dextran, carboxymethyl starch sodium, pectin, methyl cellulose, ethyl cellulose, xanthan gum, gum arabic, casein, agar, polyethylene glycol, diglycerin, glycerin, propylene glycol, vaseline, paraffin, stearyl alcohol, stearic acid, mannitol, sorbitol, lactose, a pharmaceutically acceptable surfactant, a buffer, an emulsifier, a suspending agent, a soothing agent, a stabilizer and the like.

Actually used additives are selected from the aforementioned examples singly or as an appropriate combination in accordance with the dosage form of a treatment agent of the present invention, but the additives are not limited to these examples. When the cell preparation is used, for example, as a preparation for injection, a purified antibody is dissolved in a solvent, such as a saline, a buffer or a glucose solution, and an adsorption preventing agent such as Tween 80, Tween 20 or gelatin is added to the resulting solution.

5.3 Cell Sheet

When the corneal endothelial progenitor cell population obtained by the method of the present invention is cultured on a suitable polymer membrane (carrier) to be differentiation-induced to corneal endothelial cells, or when the corneal endothelial cell population obtained by the method described in item 3. above is cultured on a suitable polymer membrane (carrier), a corneal endothelial cell sheet can be produced.

Examples of the polymer membrane to be used include membranes of biopolymers such as collagen, atelocollagen, alkali-treated collagen, gelatin, keratin, hyaluronate, glycosaminoglycan (such as chondroitin sulfate, dermatan sulfate, hyaluronate, heparan sulfate, heparin or keratan sulfate), proteoglycan, alginate, chitosan, polyamino acids (polylactic acid), and cellulose; and temperature responsive polymers such as (meth)acrylamide compounds, N-(or N,N-di)alkyl-substituted (meth)acrylamide derivatives, vinyl ether derivatives and copolymers of these.

Examples of diseases to which the administration of the cell preparation of the present invention or the transplantation of the cell sheet of the present invention obtained by the aforementioned methods is applied include corneal endothelial dysfunction including bullous keratopathy, cornea dystrophy, developmental glaucoma, Rieger's anomaly, congenital hereditary corneal endothelial dystrophy, limbal dermoid, sclerocornea, cornea shape abnormality such as keratoconus and pellucid marginal corneal degeneration, corneal cicatrization, corneal infiltration, corneal precipitation, corneal edema, corneal ulcer, eye injuries including those caused by a chemical substance or heat, eye diseases such as keratitis, corneal degeneration and corneal infection, neuroblastoma, Hirschsprung's disease, Waardenburg syndrome, localized albinism, and Recklinghausen's disease.

EXAMPLES

The present invention will now be specifically described with reference to examples, and it is noted that the present invention is not limited to these examples.

[Material and Method]

1. Culture and Maintenance of Corneal Endothelial Progenitor Cells

Medium for Establishing/Maintaining Corneal Endothelial Progenitor Cells

DMEM/F-12 (Invitrogen, basal medium)

20% KnockOUT Serum Replacement (Invitrogen, serum replacement)

2 mM L-glutamine (Invitrogen)

1% Non-Essential amino acid (Invitrogen)

100 µM 2-mercaptoethanol (Invitrogen)

4 ng/ml Basic FGF (Wako Pure Chemical Industries, Ltd.)

Coating Agent for Use in Culture of Corneal Endothelial Progenitor Cells

Matrigel™ hESC-qualified Matrix (BD)

Matrigel™ molten on ice or at 4° C. was diluted with a cooled DMEM/F12 medium (Invitrogen) 30 times, and the resultant was added to a culture dish, followed by incubation performed at 37° C. for 1 hour, so as to coat the culture dish.

Laminin 511 (Veritas Corporation)

Laminin 511 was diluted with PBS to a concentration of 20 µg/ml, and the resultant was added to a culture dish, followed by incubation performed at 37° C. for 2 hours, so as to coat the culture dish. After washing the coated culture dish twice with PBS and twice with a medium to be used, the medium was added to the culture dish.

Preparation of Corneal Endothelial Progenitor Cells from Human Corneal Endothelial Tissue Human corneal endothelial tissue was ablated together with a Descemet's membrane, was put in a 3.5 cm culture dish holding DMEM (Invitrogen) containing 10 µM Y-27632 (Wako Pure Chemical Industries, Ltd., ROCK inhibitor; apoptosis inhibitor), and the resultant was maintained at 37° C. for 30 minutes.

Subsequently, 1 ml of Stem Pro Accutase (Invitrogen, cell dissociation solution) was added thereto, followed by a treatment at 37° C. for 30 minutes, 4 ml of DMEM (Invitrogen) was added thereto, and the resultant was transferred into a 15 ml tube. The tube was centrifuged at 1,500 rpm for 5 minutes, a supernatant was aspirated, and 200 µl of the above-described medium was added thereto. The resultant was seeded in a culture dish coated with Matrigel™ or Laminin 511 (at a seeding density of 50 to 1000 cells/cm$^2$) and was cultured with the medium exchanged every 2 to 3 days. Colonies appeared in approximately 7 to 14 days.

Passage of Corneal Endothelial Progenitor Cells

To cells cultured to be sub-confluent, Y-27632 (Wako Chemical Industries, Ltd., apoptosis inhibitor) was added to a final concentration of 10 µM, and the resultant was allowed to stand at 37° C. for 60 minutes. The resulting cells were washed with PBS once, 0.25 ml of Stem Pro Accutase (Invitrogen, cell dissociation solution) was added thereto, and the resultant was allowed to stand at room temperature for 2 to 5 minutes.

A 5-fold volume of medium was added thereto, and the resultant was transferred into a 15 ml tube. The tube was centrifuged at 1,000 rpm for 5 minutes, a supernatant was aspirated, and the medium was added thereto. The resultant was seeded in a culture dish coated with Matrigel™ or Laminin 511 (at a seeding density of 5,000 to 20,000 cells/cm$^2$) and was cultured with the medium exchanged every 2 to 3 days.

2. Differentiation Induction from Corneal Endothelial Progenitor Cells to Corneal Endothelial Stem Cells Medium used for differentiation induction from corneal endothelial progenitor cells to mature corneal endothelial cells DMEM low-glucose (Medical & Biological Laboratories Co., Ltd.)

10% FBS (Japan Bio Serum)

2 mM L-glutamine (Invitrogen)

1% Penicillin-Streptomycin (Invitrogen)

Coating Agent for Use in Differentiation Induction to Corneal Endothelial Cells

FNC Coating Mix (Athena ES)

FNC coating mix (a coating agent containing fibronectin and type I collagen) was added to a culture dish and allowed to stand at room temperature for 30 seconds.

Differentiation from Corneal Endothelial Progenitor Cells to Mature Corneal Endothelial Cells Y-27632 (Wako Pure Chemical Industries Co., Ltd.) was added to the corneal endothelial progenitor cells cultured by the above-described method to a final concentration of 10 µM, so as to perform a treatment at 37° C. for 60 minutes. The resultant was washed with PBS once, and 0.25 ml of Stem Pro Accutase (Invitrogen, cell dissociation solution) was added thereto, followed by incubation performed at room temperature for 2 to 5 minutes.

A 5-fold volume of medium was added thereto, and the resultant was transferred into a 15 ml tube. The tube was centrifuged at 1,000 rpm for 5 minutes, a supernatant was aspirated, and the medium was added thereto. The resultant was seeded in a culture dish coated with FNC coating mix or on an atelocollagen sheet (AteloCell, KOKEN Co., Ltd.) (at a seeding density of 3,000 to 5,000 cells/cm²) and was cultured with the medium exchanged every 2 to 3 days. In 1 to 4 weeks, cells in a corneal endothelium-like shape (cobblestone like shape) appeared.

Medium Used for Maintaining Mature Corneal Endothelial Cells

DMEM low-glucose (Medical & Biological Laboratories Co., Ltd., basal medium)

10% FBS (Japan Bio Serum)

2 mM L-glutamine (Invitrogen)

1% Penicillin-Streptomycin (Invitrogen)

2 ng/ml bFGF (Invitrogen)

4. Corneal Endothelial Cells Obtained by Known Method

Cells were isolated from corneal tissue in the same manner as described in item 1. above, and the cells were cultured by a known method (mentioned above, Yokoo et al., IVOS, 2005). Specifically, the isolated corneal endothelial cells were seeded in a non-adherent culture dish by using a medium containing DMEM/F12, B27 supplement, 40 ng/ml bFGF and 20 ng/ml EGF. The cells were cultured for 10 days in total with 40 ng/ml bFGF and 20 ng/ml EGF added every 2 days.

5. Real-Time PCR

RNA Extraction

RNA was extracted from the cells by using RNeasy Micro Plus kit (QIAGEN).

cDNA Synthesis

From the RNA obtained as described above, cDNA was prepared by using SuperScript III First-Strand Synthesis SuperMix for qRT-PCR (Invitrogen).

Real-Time PCR

Real-time PCR was performed by using TaqMan Fast Universal PCR Master Mix (Applied Biosystems) and TaqMan probes (Applied Biosystems) shown in Table 1 and by using 7500 Fast real-time PCR system (Applied Biosystems). Data analysis was performed by a ΔΔ Ct method with GAPDH used as an endogenous control.

TABLE 1

| List of TaqMan probes | |
| --- | --- |
| Gene | Assay ID |
| GAPDH | Hs99999905_m1 |
| COL8A2 | Hs00697025_m1 |
| p75 | Hs00609976_m1 |
| FOXC2 | Hs00270951_s1 |
| SOX9 | Hs00165814_m1 |
| N-cadherin | Hs00983062_m1 |

6. Immunostaining

The corneal endothelial progenitor cells or the corneal endothelial cells prepared as described above were fixed with 4% paraformaldehyde (Wako Pure Chemical Industries Co., Ltd.) at room temperature for 30 minutes or with cooled methanol (Wako Pure Chemical Industries Co., Ltd.) at −30° C. for 30 minutes. The resultant was washed with Tris buffer (TBS, Takara Bio Inc.) twice, followed by a treatment with 5% NST (whose composition is shown in Table 2) at room temperature for 1 hour.

TABLE 2

| NST composition | | |
| --- | --- | --- |
|  | 5% NST | 1% NST |
| Normal Donkey Serum | 5% | 1% |
| Triton-X 100 | 0.3% | 0.3% |

A primary antibody, adjusted to each optimum concentration with 1% NST, was incubated overnight at 4° C. (see Table 3), and the resultant was washed with TBS three times. Subsequently, a secondary antibody (Invitrogen, AlexaFluor 488 or 568 conjugated anti-IgG antibody), which had been diluted with 1% NST 200 times, was added thereto, and the resultant was incubated at room temperature for 2 hours.

Nuclear staining was performed by using 0.2 mg/ml Hoechst 33342 (Invitrogen), and the resultant was washed with TBS three times and then mounted in a water soluble mounting medium (Perma Fluor, Thermo Fisher Scientific K.K.). The mounted cells were observed with a fluorescence microscope (Axio observer A1, Zeiss) and were imaged by using AxioVision (Zeiss).

TABLE 3

| List of antibodies | | |
| --- | --- | --- |
|  | Catalog No. | Dilution |
| N-cadherin | Santa Cruz, sc-7939 | 1:100 |
| ZO-1 | invitrogen, 339100 | 1:100 |
| Ki-67 | abcam, ab833 | 1:400 |
| Na+/K+-ATPase | Millipore, 05-369 | 1:100 |

7. Alizarin Staining

Alizarin red S (Wako Pure Chemical Industries Co., Ltd.) was adjusted to have 0.9% NaCl (pH 4.2). The cells were dyed with the stain for 5 minutes, then, fixed with 4% paraformaldehyde, and observed with a microscope.

8. Measurement of Pump Function

The pump function was measured by using an Ussing chamber. An induced corneal endothelial cell sheet cultured on atelocollagen was incubated with Krebs-Ringer buffer (120.7 mM NaCl, 24 mM $NaHCO_3$, 4.6 mM KCl, 0.7 mM $Na_2HPO_4$, 0.5 mM $MgCl_2$, 10 mM glucose, pH 7.4). An Ussing chamber system available from WPI was used. A $Na^+/K^+$-ATPase inhibitor, 1 mM ouabain (Sigma) was added thereto, and a short-circuit current was calculated.

9. Transplantation to Rabbit Corneal Endothelial Wound Model

As a rabbit corneal endothelial wound model, a corneal endothelium of one eye of a rabbit was exfoliated by a cryo method. After 1 week, the induced corneal endothelial sheet was adhered onto a corneal endothelial surface by descemet's stripping automated endothelial keratoplasty (DSAEK), and was tightly fit by injecting air. The corneal thickness was measured over time with a pachymeter (SP-100, Tomey), and an anterior eye image was observed with a slit lamp (AlP-20, Topcon Corporation).

[Results]

(1) Cells Obtained by Method of the Present Invention

Cells isolated from human corneal endothelial tissue (number of endothelial cells: approximately 1 to $4 \times 10^4$ cells) were cultured at a density of 50 to 1000 cells/cm² under serum-free condition, and colonies appeared in approximately 7 to 14 days of the culture (incidence: approximately 0.1%: approximately 10 to 40 cells per eye).

Figure 1:
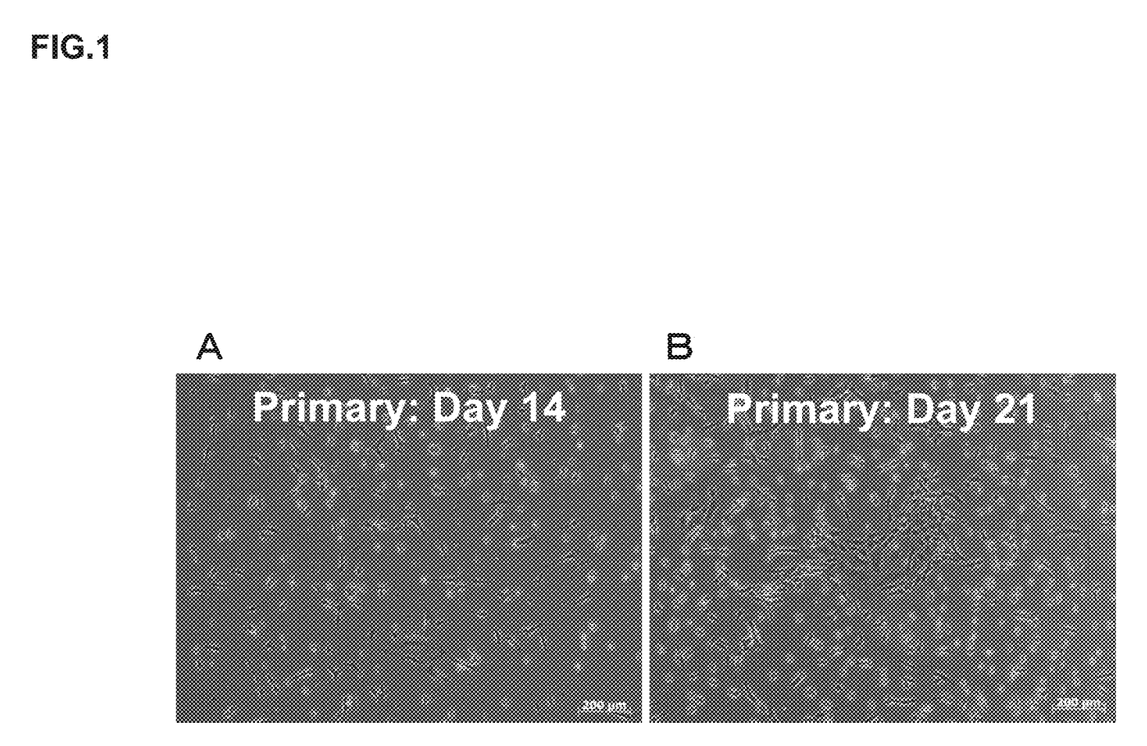

The shape of cells grown from the corneal endothelial tissue by the method of the present invention was extremely similar to that of neural crest cells induced from iPS cells, and hence, it was suggested that these cells could possibly be corneal endothelial progenitor cells (FIG. 1).

(2) Analysis of Marker Gene of Corneal Endothelial Progenitor Cells

Figure 2:
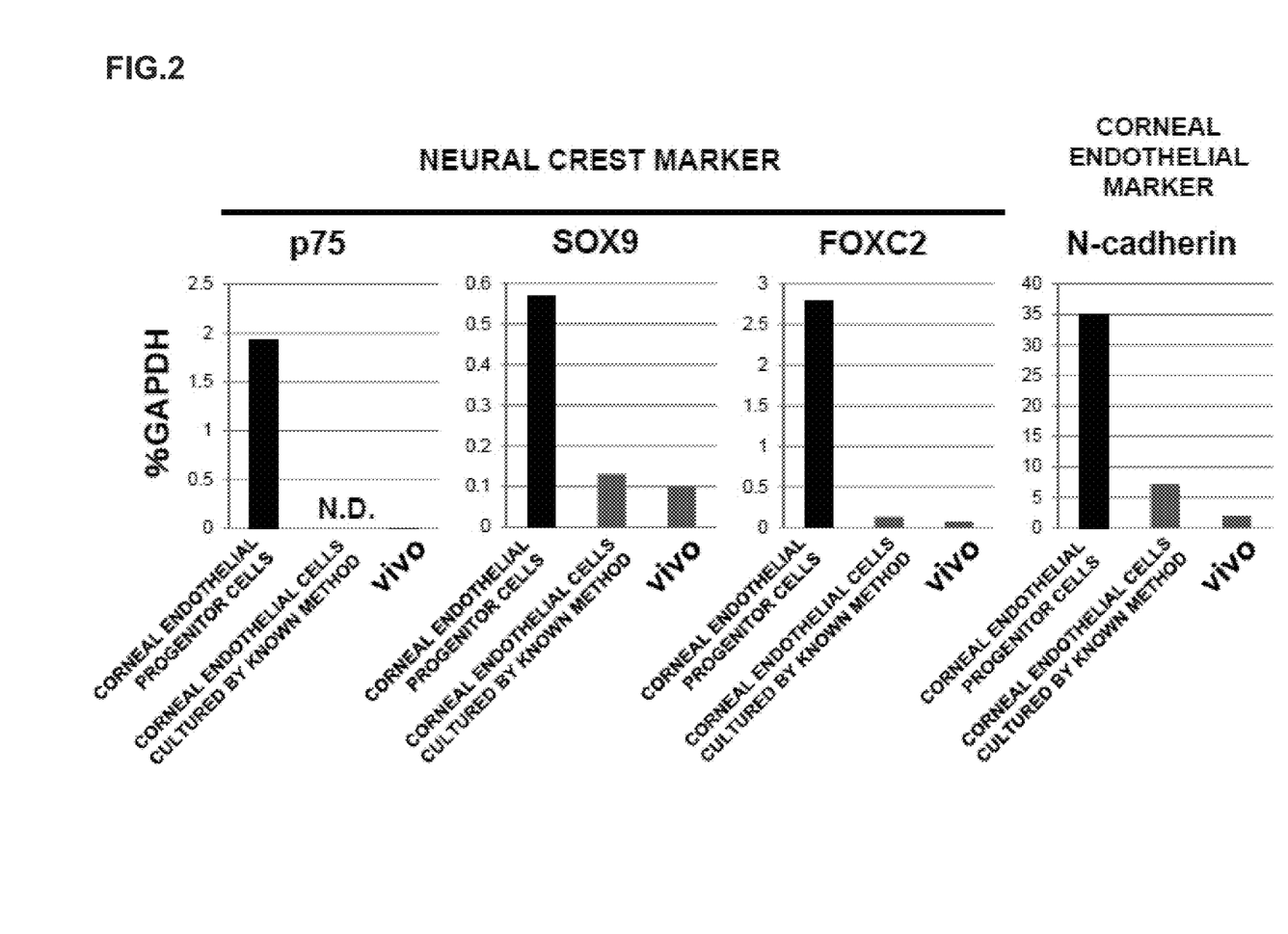
FIG. 2 illustrates expression of neural crest markers p75, SOX9 and FOXC2 and a corneal endothelial marker N-cadherin in corneal endothelial progenitor cells obtained by the method of the present invention. In each graph, the expressions in the corneal endothelial progenitor cells obtained by the method of the present invention, cells obtained by a known method, and corneal endothelial cells present in vivo are illustrated in this order from the left.

In the corneal endothelial progenitor cells obtained by the method of the present invention, the expression of the neural crest markers p75, SOX9 and FOXC2 derived from corneal endothelial generation, and the expression of N-cadherin, that is, one of the corneal endothelial markers, were increased as compared with those in endothelial cells cultured by a known method and in cells present in vivo (FIG. 2).

Figure 3:
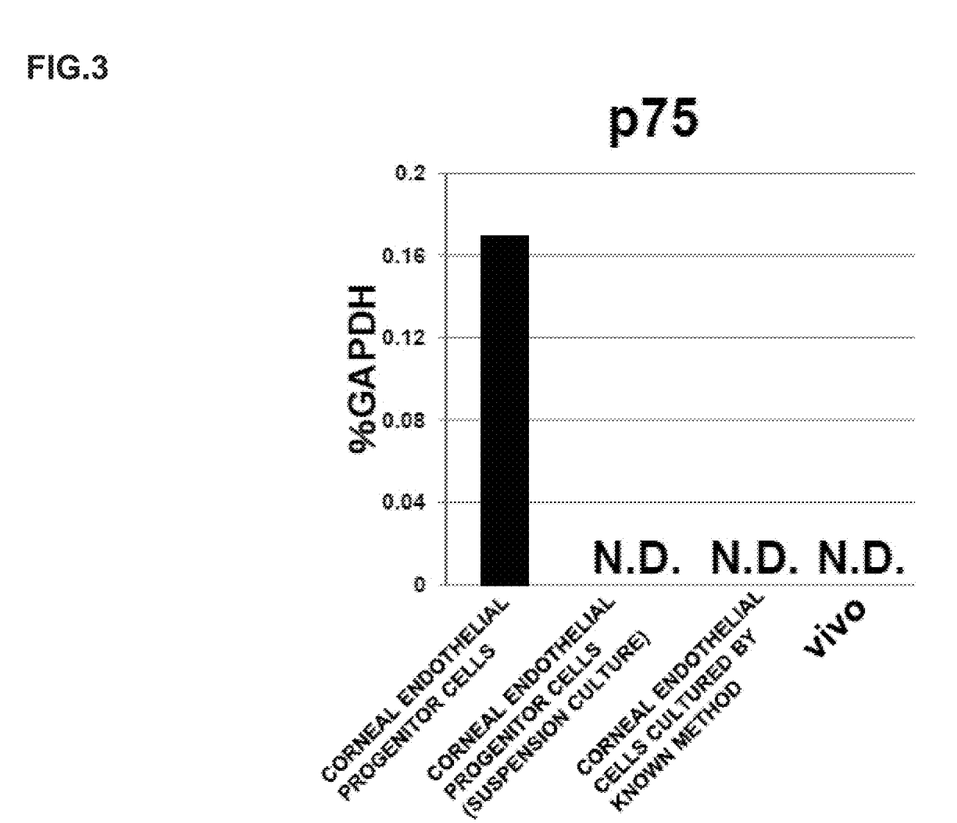
FIG. 3 is a graph illustrating an expression level of p75 in the corneal endothelial progenitor cells obtained by the method of the present invention compared with those attained in other cells. In this graph, expression levels attained in the corneal endothelial progenitor cells obtained by the method of the present invention, cells obtained by suspension culture instead of the method of the present invention, cells obtained by a known method and corneal endothelial cells present in vivo are illustrated in this order from the left.

(3) Comparison Between Corneal Endothelial Progenitor Cells and Cells Obtained by Known Method Although p75 was not expressed in cells obtained from corneal endothelial tissue by a known method or cells simply isolated from an organism (in vivo), p75 was expressed in the corneal endothelial stem cells/progenitor cells obtained by the method of the present invention (FIG. 3). P75 (CD271/NGFR) is a marker expressed in merely stem cells, including neural crest stem cells, present in vivo in a small number, and is used as an index of undifferentiation. These results reveal that corneal endothelial progenitor cells can be grown in a more undifferentiated state by the method of the present invention.

Furthermore, when the suspension culture (mentioned above, Yokoo et al., IVOS, 2005), that is, a known culture method for corneal endothelial progenitor cells, was employed, p75 was not expressed in resulting cells (FIG. 3). This reveals that corneal progenitor cells in a more undifferentiated state can be isolated and grown by the method of the present invention than by the known method.

(4) Proliferation Ability of Corneal Endothelial Progenitor Cells

Figure 4:
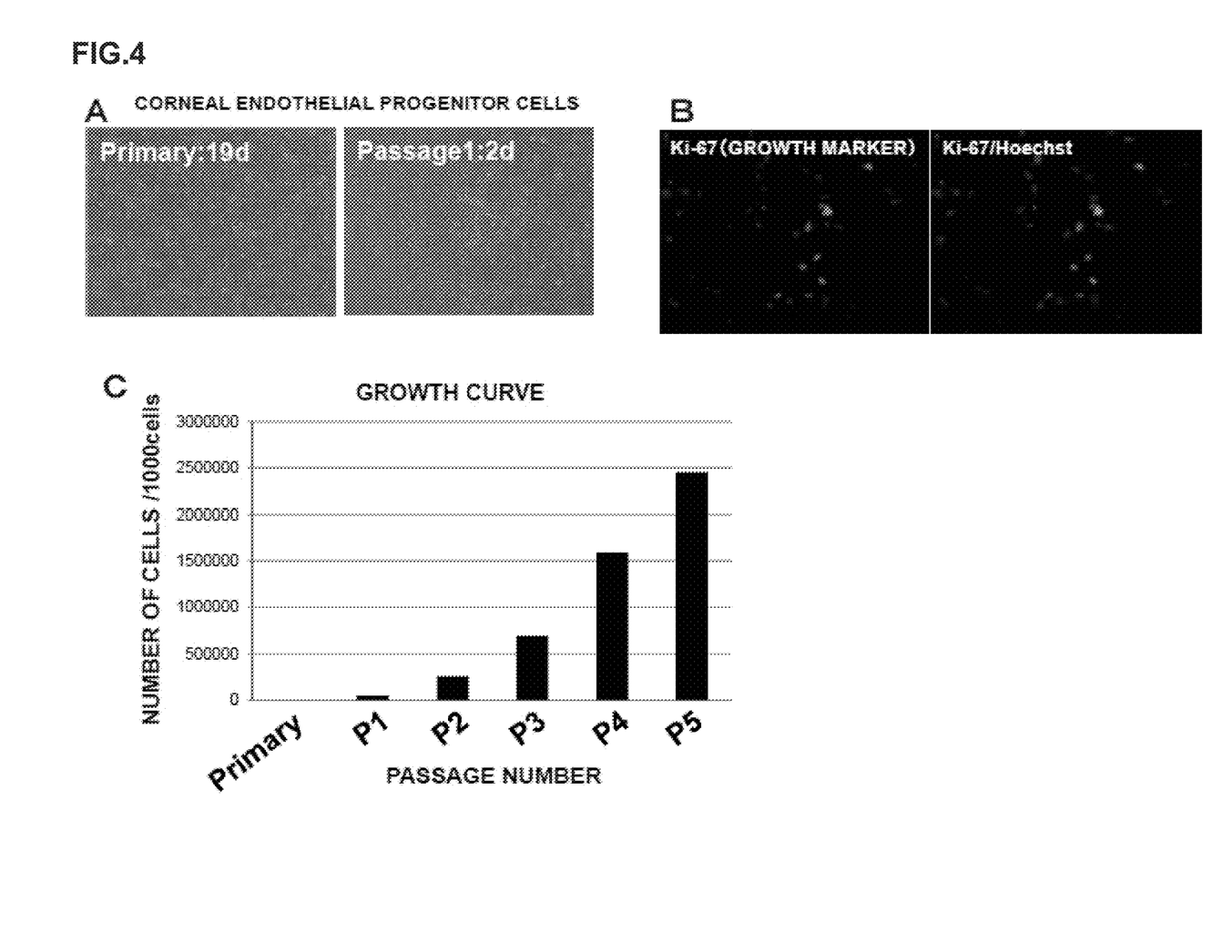
FIG. 4A illustrates photographs, taken on the second day of culture, of primary culture cells (left) and first passage cells (right)
FIG. 4B illustrates expression of a growth marker Ki-67 (specifically, a chromatic figure of Ki-67 (left) and a chromatic figure of Ki-67 and nuclear stain (right))
FIG. 4C illustrates proliferation abilities of respective passage cells (a growth curve).

In the corneal endothelial progenitor cells obtained by the method of the present invention, the growth marker was expressed (FIG. 4B). Besides, a single cell could be grown to $10^8$ cells at most through repeated culture passages (FIG. 4C). This means that $8\times10^4$ cell sheets can be theoretically prepared at most from one donor. On the contrary, the cells obtained by the known method are changed in the cell form and degraded in the proliferation ability, and hence it is difficult to repeat culture passages (mentioned above, Yokoo et al., IVOS, 2005).

Figure 5:
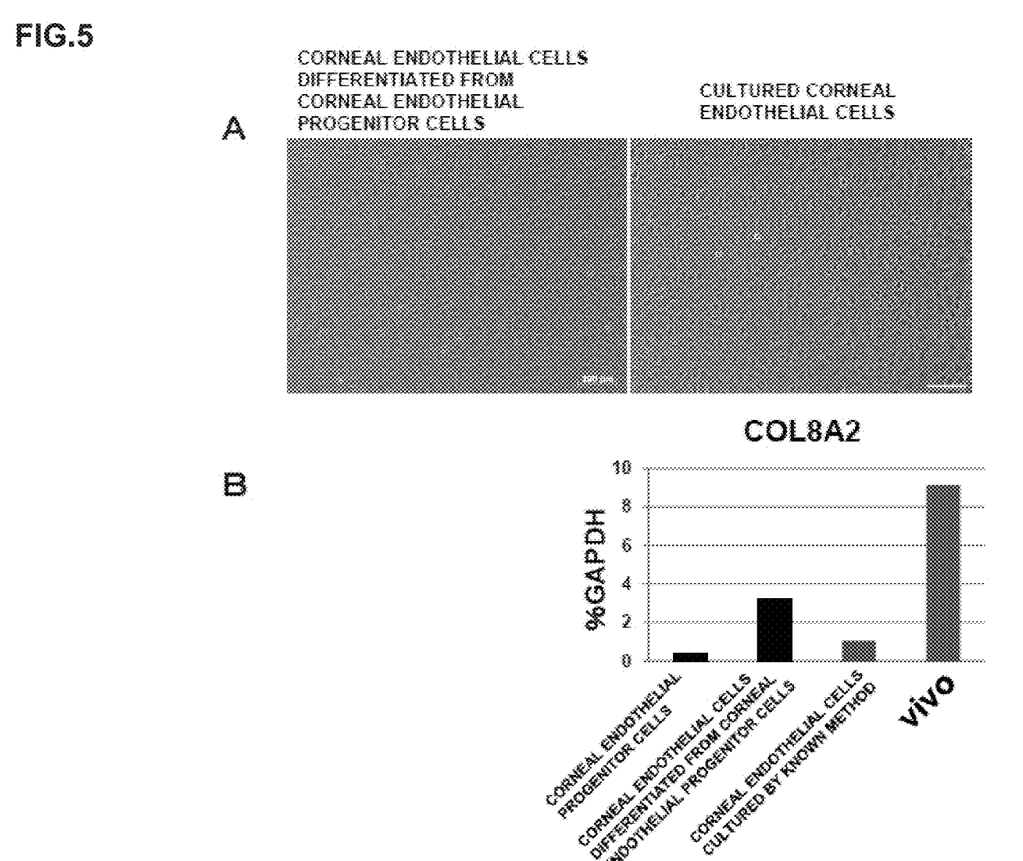

(5) Differentiation Induction from Corneal Endothelial Progenitor Cells to Corneal Endothelial Cells The corneal endothelial cells differentiated from the corneal endothelial progenitor cells obtained by the method of the present invention were in a tessellated cell shape (FIG. 5A), and the expression of the corneal endothelial marker, type VIII collagen (COL8A2) was increased (FIG. 5B). Based on this, it was confirmed that the corneal endothelial progenitor cells obtained by the method of the present invention can be differentiated into corneal endothelial cells.

(6) Preparation of Induced Corneal Endothelial Cell Sheet

An atelocollagen sheet is a highly safe medical collagen sheet, and is one of candidates of a carrier for the transplantation of a corneal endothelium. When the corneal endothelial cells induced from the corneal endothelial progenitor cells were seeded on an atelocollagen sheet, a transparent corneal endothelial cell sheet could be prepared (FIG. 6A), in which the cells were in a cobblestone like shape (FIGS. 6B and 6C).

(7) Analysis of Expression in Induced Corneal Endothelial Cell Sheet

Figure 6:
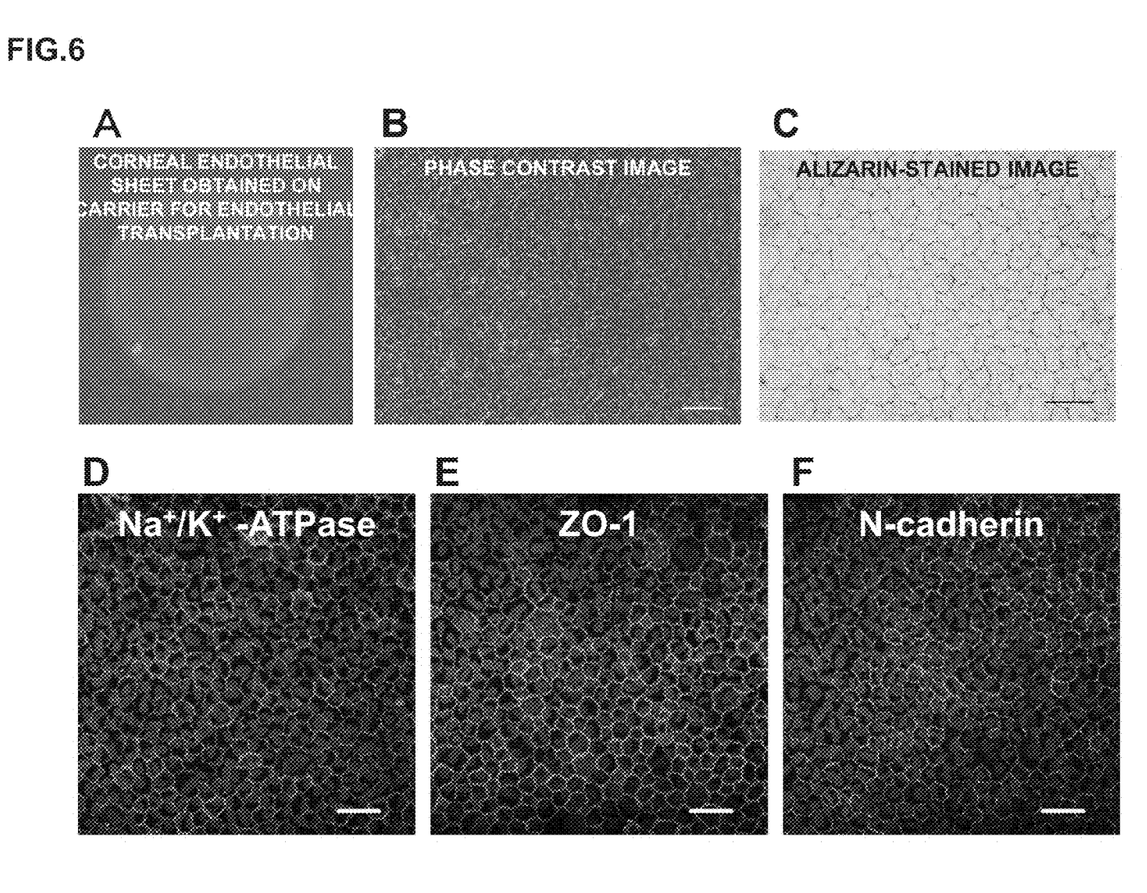

In the corneal endothelial cells re-seeded on an atelocollagen sheet, in the same manner as in the corneal endothelial cells differentiation-induced from the corneal endothelial progenitor cells, the corneal endothelium markers $Na^+/K^+$-ATPase, ZO-1 and N-cadherin were expressed (FIGS. 6D, 6E and 6F). This reveals that the induced corneal endothelial cell sheet contains mature corneal endothelial cells and is usable as a material for the tissue engineering.

(8) Analysis of Pump Function of Induced Corneal Endothelial Cell Sheet

Figure 7:
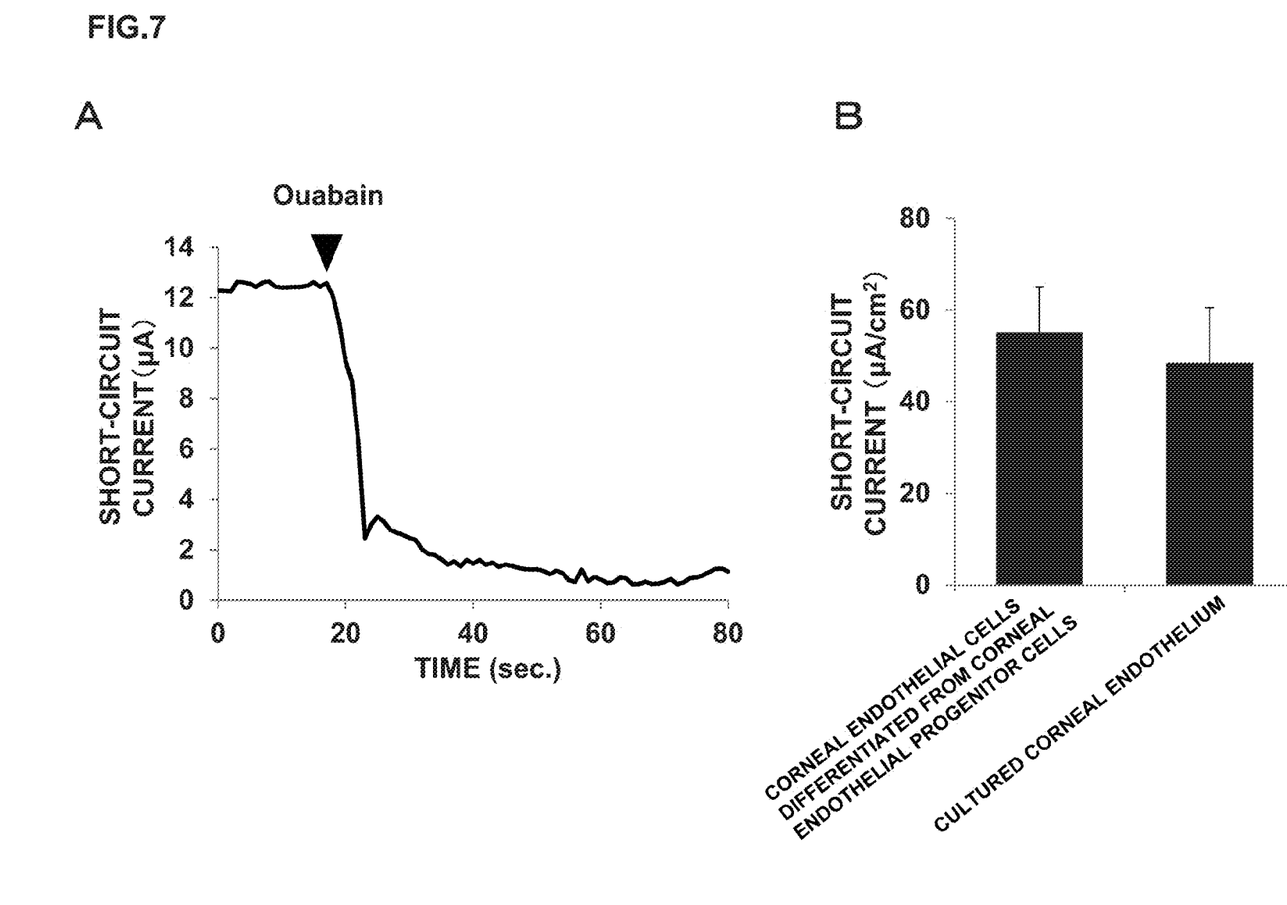

The induced corneal endothelial cell sheet obtained by the present invention was analyzed for the pump function by using an Ussing chamber (FIG. 7A). As a result, it was found that the pump function was equivalent to that of cultured corneal endothelial cells (FIG. 7B).

Figure 8:
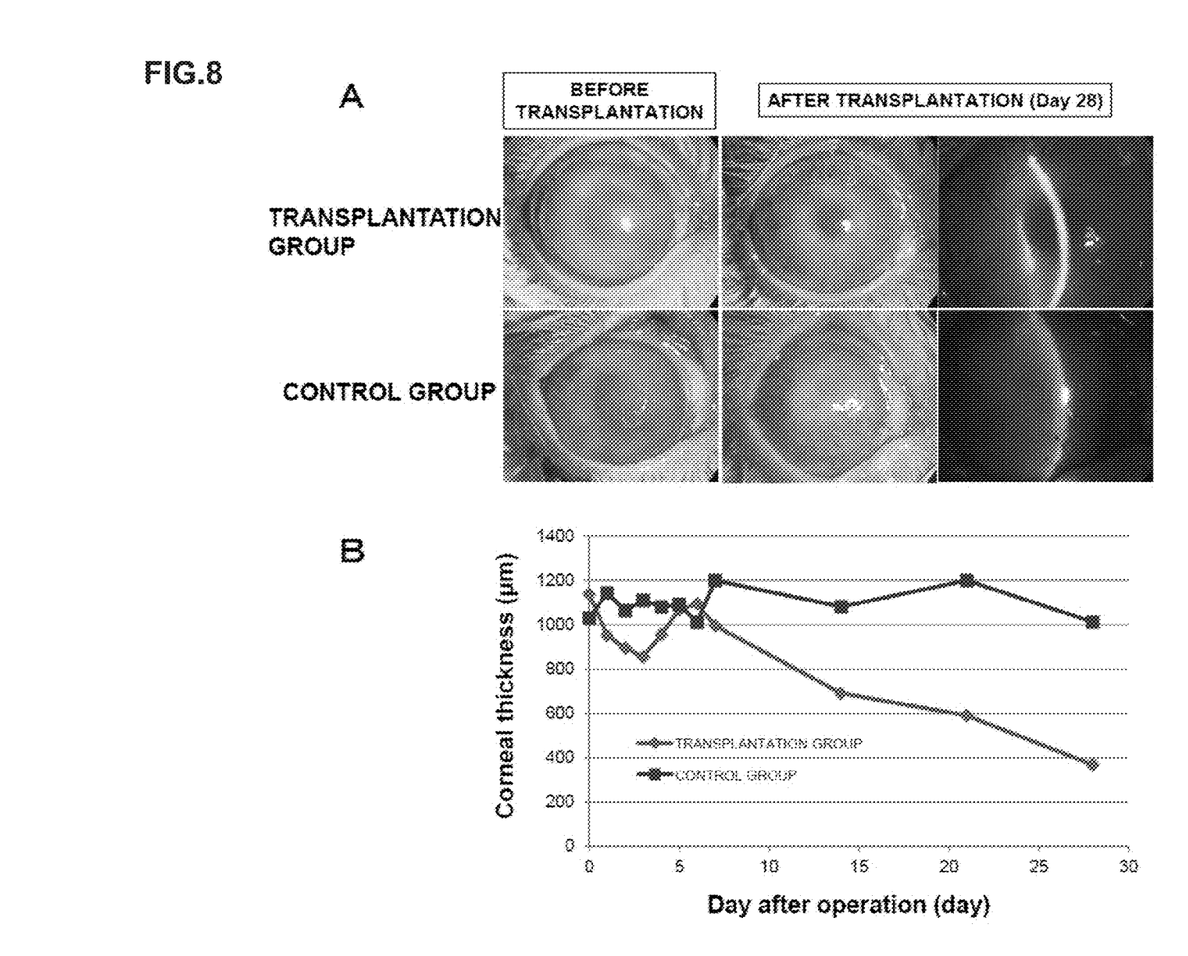
FIG. 8A illustrates verification results of transparency of a cornea (of a transplantation group shown in an upper portion and a control group shown in a lower portion, both with an image obtained before the transplantation shown on the left side and images obtained 28 days after the transplantation shown in the middle and on the right side)
FIG. 8B illustrates verification results of improvement in the corneal thickness (with results of the transplantation group shown with -♦- and those of the control group shown with -■-).

(9) Transplantation Experiment of Induced Corneal Endothelial Cell Sheet to Rabbit Endothelial Wound Model When the induced corneal endothelial cell sheet obtained by the present invention was transplanted to a rabbit corneal endothelial wound model, the corneal thickness was remarkably reduced from two weeks after the transplantation as compared with that of a control group in which atelocollagen alone was transplanted (FIGS. 8A and 8B). This reveals that the induced corneal endothelial cell sheet contains mature corneal endothelial cells and is usable as a material for the tissue engineering.

CONCLUSION

It was confirmed that corneal endothelial tissue-derived cells can be grown in a more undifferentiated state (positive for p75, FOXC2 and SOX9) by the method of the present invention. The thus obtained corneal endothelial progenitor cells had high proliferation ability, and hence, approximately 330 corneal endothelial cell sheets could be theoretically prepared from one donor. It was confirmed that these cells are corneal endothelial progenitor cells having differentiation ability to mature corneal endothelial cells.

INDUSTRIAL APPLICABILITY

According to the present invention, corneal endothelial tissue-derived cells can be grown while retaining an undifferentiated state. In other words, more undifferentiated corneal endothelial progenitor cells having high proliferation ability can be selectively grown from corneal endothelial tissue-derived cells. A corneal endothelial progenitor cell population obtained by the present invention can be differentiation-induced into mature corneal endothelial cells by culture performed under suitable conditions. Accordingly, the present invention is applicable as fundamental technology for tissue engineering for treating, for example, bullous keratopathy.

It is noted that all literature, patents and patent applications cited herein are hereby incorporated by reference.

The invention claimed is:
1. A method for preparing corneal endothelial progenitor cells comprising:
    a step (a) of isolating cells dissociated from corneal endothelial cell tissue, wherein the corneal endothelial cell tissue had previously been incubated in a culture medium comprising a ROCK inhibitor; and
    a step (b) of cultivating the isolated cells of step (a) at an initial seeding density of 20 to 2000 cells/cm$^2$ by adher- ent cultivation in a serum-free medium, thereby obtaining a primary cell population of the corneal endothelial progenitor cells.

2. The method according to claim 1, wherein the cultivation of the isolated cells during step (b) is performed for at least 7 days or more.

3. The method according to claim 1, wherein the corneal endothelial progenitor cells to be obtained are positive for Ki-67 marker.

4. The method according to claim 1, wherein corneal endothelial progenitor cells characterized by being positive for p75 marker are grown.

5. The method according to claim 1, wherein corneal endothelial progenitor cells characterized by being positive for FOXC2 marker, SOX9 marker, and N-cadherin marker are grown.

6. The method according to claim 1, wherein the medium of step (b) contains at least one or more cytokines selected from bFGF, EGF, TGF, NGF and Wnt3a.

7. The method according to claim 1, wherein the medium of step (b) contains a serum replacement.

8. The method according to claim 7, wherein the medium of step (b) further contains one or more compounds selected from retinoic acid, β-mercaptoethanol, sodium pyruvate and ascorbic acid.

9. The method according to claim 1, wherein a culture vessel coated with collagen, laminin, fibronectin, MATRIGEL (TM), poly-L-ornithine/laminin, or poly-D-lysine (PDL) is used for the adherent cultivation.

10. A method for preparing corneal endothelial cells in which corneal endothelial progenitor cells are obtained comprising:
a step (a) of isolating cells dissociated from corneal endothelial cell tissue, wherein the corneal endothelial cell tissue had previously been incubated in a culture medium comprising a ROCK inhibitor;
a step (b) of cultivating the isolated cells of step (a) at an initial seeding density of 20 to 2000 cells/cm$^2$ by adherent cultivation in a serum-free medium, thereby obtaining a primary cell population of the corneal endothelial progenitor cells; and
a step (c) of inducing differentiation of the corneal endothelial progenitor cells, thereby preparing the corneal endothelial cells.

11. The method according to claim 10, wherein a serum-free medium containing TGF-$\beta_2$ or a medium containing a serum is used for the differentiation induction.

12. A method for preparing a corneal endothelial cell sheet comprising:
a step (a) of isolating cells dissociated from corneal endothelial cell tissue, wherein the corneal endothelial cell tissue had previously been incubated in a culture medium comprising a ROCK inhibitor;
a step (b) of cultivating the isolated cells of step (a) at an initial seeding density of 20 to 2000 cells/cm$^2$ by adherent cultivation in a serum-free medium, thereby obtaining a primary cell population of corneal endothelial progenitor cells; and
culturing the corneal endothelial progenitor cells, or corneal endothelial cells that are differentiation-induced from the corneal endothelial progenitor cells, on a polymer membrane, thereby obtaining the corneal endothelial cell sheet.

13. The method according to claim 12, wherein the polymer membrane contains one or more compounds selected from the group consisting of glycosaminoglycan, chondroitin sulfate, dermatan sulfate, hyaluronate, heparan sulfate, heparin, keratan sulfate, atelocollagen, alkali-treated collagen, gelatin, keratin, proteoglycan, alginate, chitosan, hyaluronate, polyamino acids, polylactic acid, cellulose, temperature responsive polymers, and temperature responsive polymers corresponding to (meth)acrylamide compounds, N-(or N,N-di)alkyl-substituted (meth)acrylamide derivatives, vinyl ether derivatives and copolymers thereof.

14. The method of claim 1, further comprising passaging the primary cell population to obtain a passaged cell population, and cultivating the passaged cell population by adherent cultivation in the serum-free medium, the corneal endothelial progenitor cells being obtained thereby.

* * * * *